(12) United States Patent
Kim et al.

(10) Patent No.: US 11,670,403 B2
(45) Date of Patent: Jun. 6, 2023

(54) METHOD AND APPARATUS FOR GENERATING CHEMICAL STRUCTURE USING NEURAL NETWORK

(71) Applicant: SAMSUNG ELECTRONICS CO., LTD., Suwon-si (KR)

(72) Inventors: Kyungdoc Kim, Seoul (KR); Youngchun Kwon, Yongin-si (KR); Misuk Kim, Seoul (KR); Jiho Yoo, Hwaseong-si (KR); Younsuk Choi, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1115 days.

(21) Appl. No.: 16/269,092

(22) Filed: Feb. 6, 2019

(65) Prior Publication Data

US 2020/0066377 A1    Feb. 27, 2020

(30) Foreign Application Priority Data

Aug. 23, 2018   (KR) .................. 10-2018-0098373

(51) Int. Cl.
| | | |
|---|---|---|
| *G01N 33/48* | (2006.01) | |
| *G01N 33/50* | (2006.01) | |
| *G16C 20/40* | (2019.01) | |
| *G16C 20/70* | (2019.01) | |
| *G06N 3/086* | (2023.01) | |

(52) U.S. Cl.
CPC .............. *G16C 20/40* (2019.02); *G06N 3/086* (2013.01); *G16C 20/70* (2019.02)

(58) Field of Classification Search
CPC ......... G16C 20/40; G16C 20/70; G06N 3/086
See application file for complete search history.

(56) References Cited

U.S. PATENT DOCUMENTS

| | | | |
|---|---|---|---|
| 2010/0010946 A1* | 1/2010 | De Winter | ............ G16B 15/30 703/1 |
| 2016/0162782 A1 | 6/2016 | Park | |
| 2018/0032663 A1 | 2/2018 | Yoo et al. | |
| 2019/0220573 A1 | 7/2019 | Kwon et al. | |

FOREIGN PATENT DOCUMENTS

| | | |
|---|---|---|
| KR | 10-2016-0069834 A | 6/2016 |
| KR | 10-2018-0014471 A | 2/2018 |
| KR | 10-2018-0056013 A | 5/2018 |
| KR | 10-2019-0087898 A | 7/2019 |
| WO | 2013175240 A1 | 11/2013 |
| WO | 2016150472 A1 | 9/2016 |

OTHER PUBLICATIONS

Communication dated Nov. 5, 2019, issued by the European Patent Office in counterpart European Application No. 19164409.5.

(Continued)

*Primary Examiner* — Russell S Negin
(74) *Attorney, Agent, or Firm* — Sughrue Mion, PLLC

(57) ABSTRACT

Generating a new chemical structure by using a neural network using an expression region that expresses a particular property in a descriptor or an image for a reference chemical structure. The new chemical structure may be generated by changing a partial structure in the reference chemical structure that corresponds to the expression region.

9 Claims, 10 Drawing Sheets

(56) References Cited

OTHER PUBLICATIONS

Venkataswamy Sorna et al. "High-Throughput Virtual Screening Identifies Novel N'-(1-Phenylethylidene)-benzohydrazides as Potent, Specific, and Reversible LSD1 Inhibitors", Journal of Medicinal Chemistry, vol. 56, 2013, (pp. 9496-9508) XP05516189.
Jaechang Lim et al. "Molecular generative model based on conditional variational autoencoder for de novo molecular design", Journal of Cheminformatics, vol. 10, No. 1, Jul. 11, 2018 (9 pages total) XP055635609.
Yinchong Yang et al. "Explaining Therapy Predictions with Layer-wise Relevance Propagation in Neural Networks", IEEE International Conference on Healthcare Informatics, Jun. 4, 2018, (pp. 152-162), XP033377136.
Marwin HS Segler et al. "Generating Focussed Molecule Libraries for Drug Discovery with Recurrent Neural Networks", Arxiv.org, Cornell University Ithaca, Jan. 5, 2017, (17 pages total) XP080739723.
Communication dated Dec. 9, 2021 by the European Patent Office in European Patent Application No. 19164409.5.
Sanchez-Lengeling, Benjamin et al., "Inverse molecular design using machine learning: Generative models for matter engineering", Frontiers in Computation, Jul. 27, 2018, vol. 361, pp. 360-365, XP055634377. (6 pages total).
Bianucci, et al., "Application of Cascade Correlation Networks for Structures to Chemistry", 2000, Applied Intelligence, vol. 12, pp. 117-146.
Pastur-Romay, et al., "Deep Artificial Neural Networks and Neuromorphic Chips for Big Data Analysis: Pharmaceutical and Bioinformatics Applications", 2016, International Journal of Molecular Sciences, vol. 17, Issue 1313, pp. 1-26.
Muller et al., "Machine Learning and AI for the sciences—Towards Understanding", Nov. 17, 2107, Center For Brains Minds + Machines, http://www.heatmapping.org/slides/2018_WCCI.pdf. (46 pages total).
Ancona et al., "Towards better understanding of gradient-based attribution methods for Deep Neural Networks", Apr. 30, 2018, International Conference on Learning Representations (ICLR), pp. 1-16.
Gregoire Montavon et al., "Methods for interpreting and understanding deep neural networks", Oct. 24, 2017, Digital Signal Processing, vol. 73, 15 pages total.
Nathan Brown et al., "A Graph-Based Genetic Algorithm and Its Applications to the Multiobjective Evolution of Median Molecules", 2004, J. Chem. Inf. Comput. Sci., vol. 44, 9 pages total.
Communication dated Jun. 22, 2022 by the Korean Intellectual Property Office for Korean Patent Application No. 10-2018-0098373.

* cited by examiner

RNN with a loop    unfolded RNN

METHOD AND APPARATUS FOR GENERATING CHEMICAL STRUCTURE USING NEURAL NETWORK

CROSS-REFERENCE TO RELATED APPLICATIONS

This application claims priority from Korean Patent Application No. 10-2018-0098373, filed on Aug. 23, 2018, in the Korean Intellectual Property Office, the disclosure of which is herein incorporated by reference in its entirety.

BACKGROUND

1. Field

The disclosure relates to methods and apparatuses for generating a chemical structure using a neural network.

2. Description of the Related Art

A neural network refers to a computational architecture that models a biological brain. With the advanced neural network technologies, various types of electronic systems have analyzed input data and generated optimized information by using neural networks.

In recent years, extensive research has been conducted into methods of selecting chemical structures to be used in material development by evaluating properties of the chemical structures using neural network technologies. Particularly, there is a need to develop methods of generating new chemical structures satisfying a variety of requirements by using neural network technologies.

SUMMARY

Embodiments of the disclosure relate to methods and apparatuses for generating a chemical structure using a neural network. Also, provided are computer-readable recording media including a program, which, when executed by a computer, performs the methods. The technical problems to be solved are not limited to these as described, but there may be other technical problems.

Additional aspects will be set forth in part in the description which follows and, in part, will be apparent from the description, or may be learned by practice of the presented embodiments.

According to an aspect of an embodiment, there is provided a method of generating a chemical structure by using a neural network apparatus including: inputting a descriptor of a chemical structure to a trained neural network that generates a property value of a property of the chemical structure, the descriptor of the chemical structure representing structural characteristics of the chemical structure and the property of the chemical structure being a characteristic possessed by the chemical structure; determining an expression region for expressing the property in the descriptor, the expression region comprising a bit position in the descriptor; and generating a new chemical structure by modifying a partial structure in the chemical structure, the partial structure corresponding to the expression region.

The determining of the expression region may include determining the expression region for expressing the property in the descriptor by the trained neural network performing an interpretation process to determine whether the property value is expressed by the partial structure in the chemical structure.

The determining of the expression region may include determining the expression region for expressing the property in the descriptor by applying a layer-wise relevance propagation (LRP) technique to the trained neural network, wherein an activation function applied to a node of the trained neural network may be designated as a linear function to apply the LRP technique to the trained neural network, and a mean square error (MSE) may be designated for optimization.

The generating of the new chemical structure may include: obtaining a bit value of the bit position of the expression region in the descriptor; and generating the new chemical structure by applying a genetics algorithm to the bit value of the bit position and modifying the partial structure corresponding to the expression region.

The generating of the new chemical structure may include: generating a new first chemical structure by modifying the partial structure in the chemical structure, the partial structure corresponding to the expression region; inputting a descriptor for the new first chemical structure to the trained neural network to output a property value of a particular property for the new first chemical structure; and generating a new second chemical structure by changing a partial structure in the new first chemical structure, the partial structure corresponding to the expression region, when the property value of the particular property for the new first chemical structure is less than a preset value, and storing the new first chemical structure when the property value of the particular property for the new first chemical structure is equal to or greater than the preset value.

According to an aspect of an embodiment, there is provided a neural network apparatus configured to generate a chemical structure including: a memory configured to store at least one program; and a processor configured to drive a neural network by executing the at least one program, wherein the processor is configured to: input descriptor of a chemical structure to a trained neural network that generates a property value of a property of the chemical structure, the descriptor of the chemical structure representing structural characteristics of the chemical structure and the property of the chemical structure being a characteristic possessed by the chemical structure; determine an expression region for expressing the property in the descriptor, the expression region comprising a bit position in the descriptor; and generate a new chemical structure by modifying a partial structure in the chemical structure, the partial structure corresponding to the expression region.

According to an aspect of an embodiment, there is provided a method of generating a chemical structure by using a neural network apparatus including: inputting an image of a chemical structure to a trained neural network that generates a property value of a property of the chemical structure, the image of the chemical structure representing structural characteristics of the chemical structure and the property of the chemical structure being a characteristic possessed by the chemical structure; determining an expression region for expressing the property in the image, the expression region comprising one or more pixels in the image; and generating a new chemical structure by modifying a partial structure in the chemical structure, the partial structure corresponding to the expression region.

The determining of the expression region may include determining the expression region for expressing the property in the image by the trained neural network performing an interpretation process to determine whether the property value is expressed by the partial structure in the chemical structure.

The determining of the expression region may include determining the expression region for expressing the property in the image by applying a layer-wise relevance propagation (LRP) technique to the trained neural network, wherein an activation function applied to a node of the trained neural network may be designated as a linear function to apply the LRP technique to the trained neural network, and a mean square error (MSE) may be designated for optimization.

The generating of the new chemical structure may include: obtaining pixel values of the one or more pixels of the expression region in the image; and generating the new chemical structure by applying Gaussian noise to the pixel values of the one or more pixels and modifying the partial structure corresponding to the expression region.

The generating of the new chemical structure may include: when a plurality of expression regions expressing the particular property in the image are present, obtaining coordinate information in the image corresponding to the plurality of expression regions; calculating a center point in the image of the plurality of expression regions based on the coordinate information and obtaining a pixel value of the center point; and generating the new chemical structure by applying Gaussian noise to the pixel value and modifying the partial structure corresponding to the center point.

The generating of the new chemical structure may include: generating a new first chemical structure by modifying the partial structure in the chemical structure, the partial structure corresponding to the expression region; inputting an image for the new first chemical structure to the trained neural network to output a property value of a particular property for the new first chemical structure; and generating a new second chemical structure by changing a partial structure in the new first chemical structure, the partial structure corresponding to the expression region, when the property value of the particular property for the new first chemical structure is less than a preset value, and storing the new first chemical structure when the property value of the particular property for the new first chemical structure is equal to or greater than the preset value.

According to an aspect of an embodiment, there is provided a neural network apparatus configured to generate a chemical structure including: a memory configured to store at least one program; and a processor configured to drive a neural network by executing the at least one program, wherein the processor is configured to: input an image of a chemical structure to a trained neural network that generates a property value of a property of the reference chemical structure, the image of the chemical structure representing structural characteristics of the chemical structure and the property of the chemical structure being a characteristic possessed by the chemical structure; determine an expression region for expressing the property in the image, the expression region comprising one or more pixels in the image; and generate a new chemical structure by modifying a partial structure in the chemical structure, the partial structure corresponding to the expression region.

According to an aspect of an embodiment, there is provided a non-transitory computer-readable recording medium includes a program, which, when executed by a computer, performs any one of the methods.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
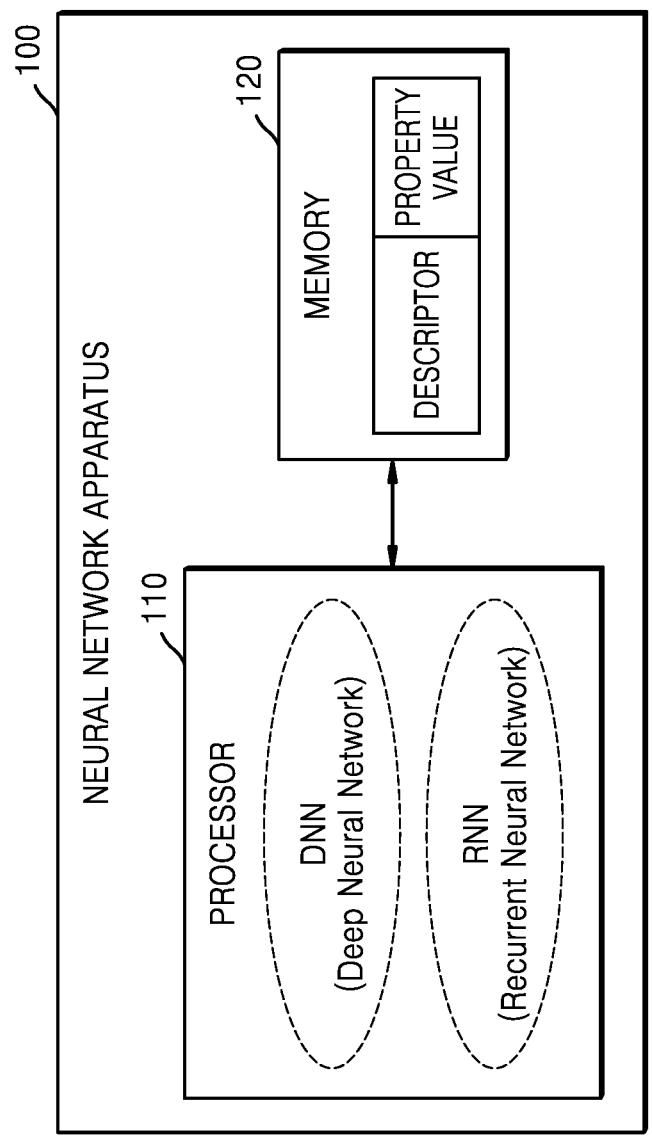
FIG. 1 is a block diagram illustrating a hardware configuration of a neural network apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list such that expressions of or similar to "at least one of a, b, and c" include: only a, only b, only c, only a and b, only b and c, only a and c, and all of a, b, and c.

The terms "according to some embodiments" or "according to an embodiment" used throughout the specification do not necessarily indicate the same embodiment.

Some embodiments of the disclosure may be represented by functional block configurations and various processing operations. Some or all of these functional blocks may be implemented using various numbers of hardware and/or software components that perform particular functions. For example, the functional blocks of the disclosure may be implemented using one or more microprocessors or circuits executing instructions to perform a given function. Also, for example, the functional blocks of the disclosure may be implemented in various programming or scripting languages. The functional blocks may be implemented with algorithms executed by one or more processors. The disclosure may also employ conventional techniques for electronic configuration, signal processing, and/or data processing. The terms "mechanism", "element", "unit" and "configuration" may be used in a broad sense and are not limited to mechanical and physical configurations.

Also, connection lines or connection members between the components illustrated in the drawings are merely illustrative of functional connections and/or physical or circuit connections. In actual devices, connections between the components may be represented by various functional connections, physical connections, or circuit connections that may be replaced or added.

Meanwhile, with respect to the terms used herein, a descriptor that is data used in a neural network system refers to an indicator value used to describe structural characteristics of a chemical structure and may be acquired by performing a relatively simple computation on a given chemical structure. According to an embodiment, a descriptor may include a molecular structure fingerprint indicating whether a particular partial structure is included (e.g., Morgan fingerprint and extended connectivity fingerprint (ECFP)). Also, the descriptor may be a quantitative structure-property relationship (QSPR) model configured with a value that may be immediately calculated from a given chemical structure, for example, a molecular weight or the number of partial structures (e.g., rings) included in a molecular structure.

In addition, a property refers to a characteristic possessed by a chemical structure and may be a real number value measured by an experiment or calculated by a simulation. For example, when the chemical structure is used as a display material, the property of the chemical structure may be expressed by a transmission wavelength, an emission wavelength, or the like with respect to light. When the chemical structure is used as a battery material, the property of the chemical structure may be a voltage. Unlike the descriptor, calculation of the property may require complex simulations that necessitate additional calculation and computation beyond similar simulations for the descriptor.

Also, a structure refers to an atomic level structure of a chemical structure. In order to derive a property by performing First Principles Calculation, the structure is required to be expressed at an atomic level. Thus, an atomic level structure needs to be derived to generate a novel chemical structure. The structure may be a structural formula based on atomic bonding relationships or a character string in a simple format (one-dimensional). The format of the character string expressing the structure may be a Simplified Molecular-input Line-entry System (SMILES) code, a Smiles Arbitrary Target Specification (SMARTS) code, an International Chemical Identifier (InChi) code, or the like.

In addition, a factor refers to an element defining the relationships among the descriptor, the property, and the structure. The factor may be determined by machine learning based on a descriptor-property-structural formula stored in a database. Thus, how relationships between the factor, the descriptor, the property, and the structural formula may be determined.

Hereinafter, embodiments of the disclosure will be described in detail with reference to the accompanying drawings.

FIG. 1 is a block diagram illustrating a hardware configuration of a neural network apparatus 100 according to an embodiment.

The neural network apparatus 100 may be implemented using various types of devices such as a personal computer (PC), a server, a mobile device, and an embedded device. Examples of the neural network apparatus 100 may include, but are not limited to, a smartphone, a tablet device, an augmented reality (AR) device, an Internet of Things (IoT) device, an autonomous vehicle, a robot, a medical device, and the like which perform speech recognition, image recognition, image classification, and the like using a neural network. Furthermore, the neural network apparatus 100 may be a dedicated hardware (HW) accelerator mounted on, connected to, or installed in the devices described above. The neural network apparatus 100 may be a hardware accelerator such as a neural processing unit (NPU), a tensor processing unit (TPU), or a neural engine, which are dedicated modules for driving a neural network, but is not limited thereto.

Referring to FIG. 1, the neural network apparatus 100 includes a processor 110 and a memory 120. FIG. 1 only illustrates components of the neural network apparatus 100 related to the embodiments of the disclosure. Thus, it is apparent to those skilled in the art that the neural network apparatus 100 may further include any other general-purpose components in addition to the components shown in FIG. 1.

The processor 110 controls the overall function for driving the neural network apparatus 100. For example, the processor 110 controls the overall operation of the neural network apparatus 100 by executing programs stored in the memory 120 of the neural network apparatus 100. The processor 110 may be implemented as a central processing unit (CPU), a graphics processing unit (GPU), an application processor (AP), or the like provided in the neural network apparatus 100, but is not limited thereto.

The memory 120 is a hardware component that stores a variety of data processed in the neural network apparatus 100. For example, the memory 120 may store data processed and to be processed by the neural network apparatus 100. The memory 120 may also store applications, drivers, and the like to be executed by the processor 110 of the neural network apparatus 100. The memory 120 may include random access memory (RAM) such as dynamic random access memory (DRAM) and static random access memory (SRAM), read-only memory (ROM), electrically erasable programmable read-only memory (EEPROM), a CD-ROM, Blue-ray or other optical disk storage, a hard disk drive (HDD), a solid state drive (SSD), or a flash memory.

The memory 120 may store a descriptor for a chemical structure and a property value numerically representing the property of the chemical structure, which match each other as one set or pair. The neural network apparatus 100 may read the descriptor and the property value corresponding thereto from the memory 120 or write the descriptor and the property value corresponding thereto in the memory 120. In an embodiment, the descriptor may include a plurality of bit values and the property value may be a value for a transmission wavelength, an emission wavelength, a voltage, or the like.

Although not shown in FIG. 1, the memory 120 may store an image for a chemical structure and a property value numerically representing the property of the chemical structure, which are associated with each other as one set or pair. In an embodiment, the image may include n×m pixels (where n and m are natural numbers). Hereinafter, the description of the descriptor applies equally to a case where the descriptor is replaced with the image.

The memory 120 may store a structure characteristic value representing a chemical structure and a descriptor and a property value, which match the structure characteristic value as one set or pair. The structure characteristic value may be a SMILES code or a SMARTS code, as a string format that expresses a chemical structure.

The processor 110 may execute instructions to implement an artificial neural network (ANN), such as a deep neural network (DNN) and a recurrent neural network (RNN).

The processor 110 may allow the DNN to learn by using a descriptor and a property value corresponding to the descriptor and may determine a factor defining the relationship between the descriptor and the property value in this process. Then, the processor 110 may output a property value corresponding to a new descriptor as output data by driving the trained DNN by using, as input data, the new descriptor not used in the learning process of the DNN.

The processor 110 may allow the RNN to learn by using a descriptor and a structure characteristic value and may determine a factor defining the relationship between the descriptor and the structure characteristic value in this process. Then, the processor 110 may output a structure characteristic value corresponding to a new descriptor as output data by driving the trained RNN by using, as input data, the new descriptor not used in the learning process of the RNN.

The neural network apparatus 100 may further include a user interface. The user interface refers to a device or software used to input data to control the neural network apparatus 100. Examples of the user interface may include, but are not limited to, a key pad, a dome switch, a touch pad (e.g., capacitive overlay type, resistive overlay type, infrared beam type, surface acoustic wave type, integral strain gauge type, and piezo electric type), a jog wheel, and a jog switch, along with a graphical user interface (GUI) that may be displayed for receiving user input.

Figure 2:
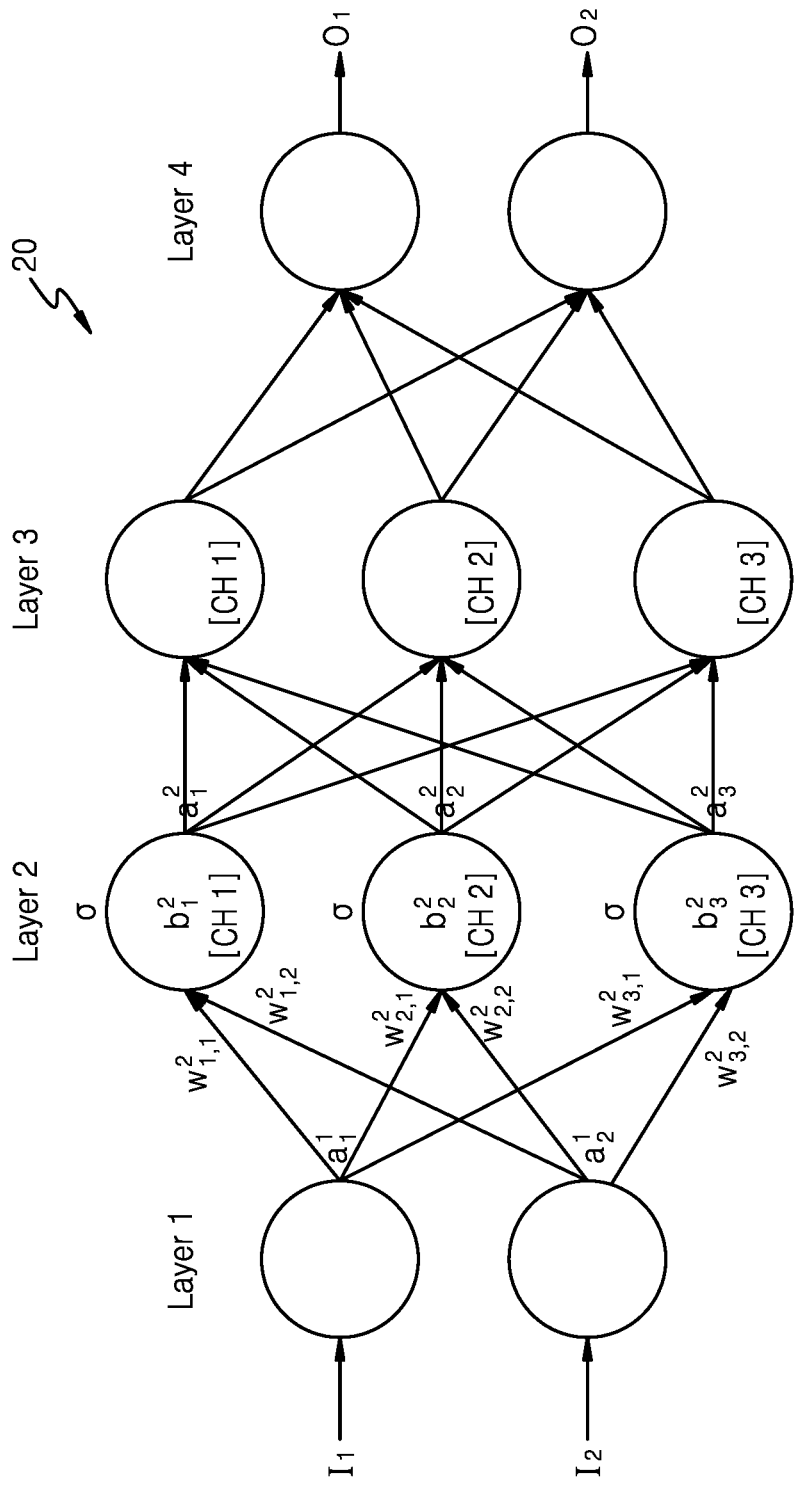
FIG. 2 is a diagram illustrating a computation performed by a deep neural network (DNN) according to an embodiment.

FIG. 2 is a diagram illustrating a computation performed by a DNN according to an embodiment.

Referring to FIG. 2, a DNN 20 may have a structure including an input layer, hidden layers, and an output layer, perform a computation based on received input data (e.g., $I_1$ and $I_2$), and generate output data (e.g., $O_1$ and $O_2$) based on a computation result.

For example, as illustrated in FIG. 2, the DNN 20 may include an input layer (Layer 1), two hidden layers (Layer 2 and Layer 3), and an output layer (Layer 4). Because the DNN 20 may include many layers to process valid information, the DNN 20 may process complex data compared to a neural network including a single layer. Meanwhile, although the DNN 20 illustrated in FIG. 2 includes 4 layers, the DNN 20 is only an example and may also include more or fewer layers and more or fewer channels than those illustrated therein. That is, the DNN 20 may have various structures of layers different from that illustrated in FIG. 2.

Each of the layers included in the DNN 20 may have a plurality of channels. The channels may respectively correspond to a plurality of artificial nodes known as neurons, processing elements (PEs), units, or similar terms. For example, as illustrated in FIG. 2, Layer 1 may include two channels (nodes), and Layers 2 and 3 may include three channels respectively. However, the layers are only examples and each of the layers included in the DNN 20 may have various numbers of channels (nodes) and interconnections to other nodes.

The channels included in each of the layers of the DNN 20 may be interconnected to process data. For example, a channel may perform a computation of data received from channels of one layer and output a computation result to channels of another layer.

Input and output of each channel may be referred to as input activation and output activation. That is, activation may be not only an output of one channel but also a parameter corresponding to an input of channels included in a successive layer. Meanwhile, each of the channels may determine an activation thereof based on activations and weights received from channels included in a previous layer. The weight is a parameter used to calculate the output activation of each channel and may be a value assigned to the relationship between channels.

Each of the channels may be processed by a computational unit or a processing element that receives an input and generates an output activation. The input-output of each channel may be mapped. For example, when σ is an activation function, $w_{jk}^i$ is a weight from a $k^{th}$ channel included in an $(i-1)^{th}$ layer to a $j^{th}$ channel included in an $i^{th}$ layer, $b_j^i$ is a bias of the $j^{th}$ channel included in the $i^{th}$ layer, and is an activation of the $j^{th}$ channel of the $i^{th}$ layer, an activation $a_j^i$ may be calculated using Equation 1 below.

$$a_j^i = \sigma\left(\sum_k (w_{jk}^j \times a_k^{i-1}) + b_j^i\right)$$ [Equation 1]

As illustrated in FIG. 2, an activation of a first channel CH1 of a second layer Layer 2 may be expressed as $a_1^2$. In addition, $a_1^2$ may have a value of $a_1^2 = \sigma(w_{1,1}^2 \times a_1^1 + w_{1,2}^2 \times a_2^1 + b_1^2)$ according to Equation 1. In Equation 1, σ denotes an activation function such as Relu, sigmoid, and tanh. As a result, the activation of a particular channel in a particular layer may denote a result obtained by passing a value of $\Sigma(w_{jk}^i \times a_k^{i-1}) + b_j^i$ through the activation function.

However, the above-described Equation 1 is only an example for describing the activation and the weight used to process data in the DNN 20 and the embodiment is not limited thereto.

In an embodiment, the neural network apparatus 100 may allow the DNN 20 to learn by using a descriptor (or image) and a property value, stored in a memory. The DNN 20 may determine a factor defining the relationship between a descriptor (or image) and a property value in a learning process using the descriptor and the property value.

That is, among Layers 1 to 4 constituting the DNN 20, the descriptor (or image) may correspond to the values of a plurality of channels (nodes) of the input layer (Layer 1), the property value may correspond to the values of a plurality of channels (nodes) of the output layer (Layer 4), and the factor may correspond to the values of a plurality of channels (nodes) of at least one hidden layer (Layers 2 and/or 3).

Then, the trained DNN 20 may be driven by receiving a new descriptor (or new image) as input data and thus may output a property value corresponding to the received new descriptor (or new image) as output data.

Figure 3:
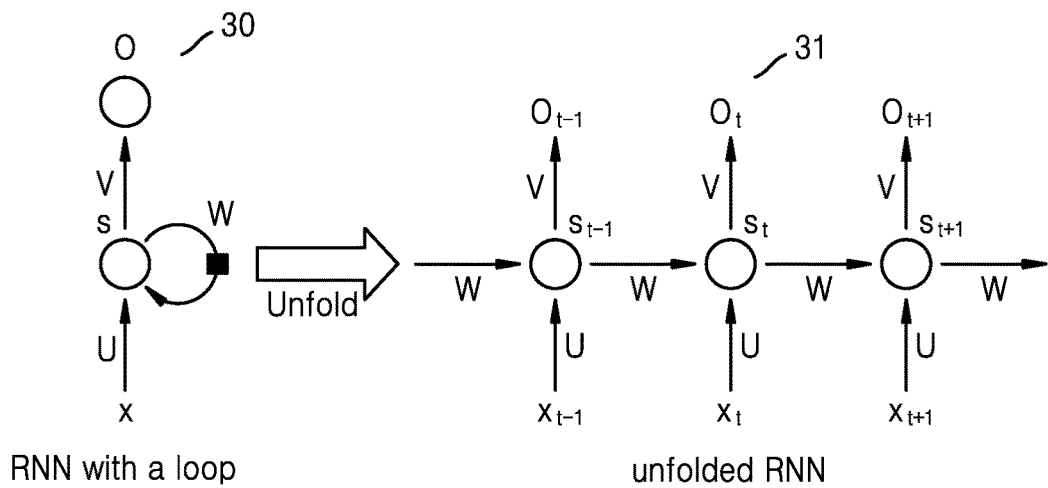
FIG. 3 is a diagram illustrating a computation performed by a recurrent neural network (RNN) according to an embodiment.

FIG. 3 is a diagram illustrating a computation performed by an RNN according to an embodiment.

Hereinafter, descriptions given above with reference to FIG. 2 will not be repeated for descriptive convenience.

An RNN 30 is a neural network that analyzes data changing with time such as time-series data and constructed by connecting a network between a reference time point t and a next time point t+1. That is, the RNN 30 is a neural network in which a temporal aspect is considered and capable of effectively learning a pattern from data sequentially input or data input with a sequence of features by modifying a model to allow a recursive input to a hidden layer of the neural network.

Referring to FIG. 3, a node s constituting a hidden layer of the RNN 30 is illustrated. The node s may perform a computation based on input data x and generate output data o. The RNN 30 may iteratively apply the same task to all sequences and a final output result of the node s is affected by a result of a previous calculation.

An RNN 31 is an unfolded RNN 30 with a loop. The term "unfold" with respect to the RNN 30 refers to expressing the RNN 30 for the entire sequence. In the RNN 31, $x_t$ is an input value at a time step t, and $s_t$ is a hidden state at the time step t. The term $s_t$ may be expressed by Equation 2 below. In Equation 2, a tanh or Relu function may be used as function f. The term $s_{-1}$ to calculate a first hidden state may generally be initialized to 0. In addition, in the RNN 31, of is an output value at the time step t.

$$s_t = f(U_{x_t} + W_{s_{t-1}})$$ [Equation 2]

Here, $s_t$ is a memory portion of the network and stores information on events at previous time steps. The output value of depends only on the memory of the current time step t.

Meanwhile, unlike the existing neural network structure in which the parameters are different from each other, the RNN 31 shares the parameters U, V, and W for all time steps. That is, because each step of the RNN 31 performs almost the same calculation except for an input value, the number of parameters to be learned may be reduced.

In an embodiment, the neural network apparatus 100 may allow the RNN 31 to learn by using a descriptor (or image) and a property value, stored in a memory. Alternatively, the neural network apparatus 100 may allow the RNN 31 to learn by using a factor and a property value, determined in a learning process of the DNN 20.

For example, when W of the RNN 31 is a factor determined in a learning process of the DNN 20 and a structure characteristic value represented by a SMILES code is "ABCD", $O_{t-1}$ and $x_t$ may be "ABC", and $O_t$ and $x_{t+1}$ may be "BCD". Then, a SMILES code in each time step may be aggregated to output one SMILES code "ABCDEFG", i.e., a structure characteristic value, as output data.

Then, the trained RNN 31 may be driven by receiving a new descriptor (or new image) as input data and thus may output a structure characteristic value corresponding to the received new descriptor (or new image) as output data. Alternatively, the trained RNN 31 may be driven by receiving a factor for a new descriptor (or new image) as input data and thus may output a structure characteristic value corresponding to the new descriptor (or new image) as output data.

Figure 4:
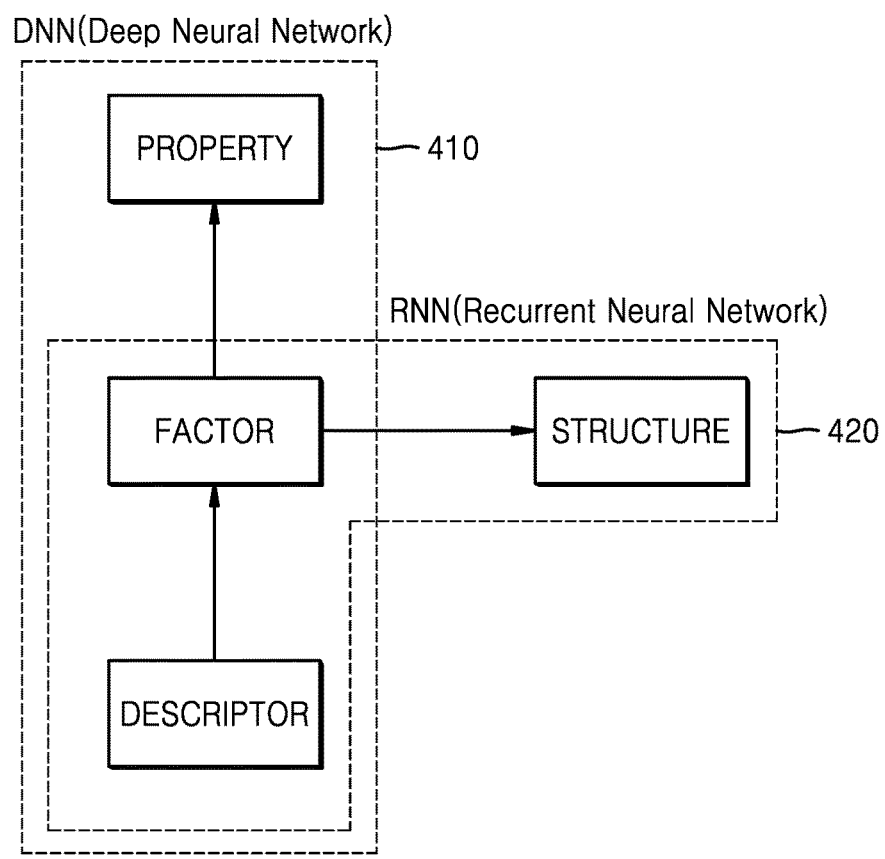
FIG. 4 is a conceptual diagram illustrating a neural network system for generating a chemical structure according to an embodiment.

FIG. 4 is a conceptual diagram illustrating a neural network system for generating a chemical structure according to an embodiment.

Referring to FIG. 4, a neural network system configured to generate a chemical structure by using a DNN 410 and an RNN 420 is illustrated.

A descriptor that is data used in the neural network system may be represented by an ECFP as an indicator value used to represent structural characteristics of a chemical structure. A property refers to a characteristic possessed by a chemical structure and may be a real number value indicating a transmission wavelength and an emission wavelength with respect to light. A structure refers to an atomic level structure of a chemical structure and may be represented by a SMILES code. For example, a structural formula may be expressed according to a SMILES code, as shown in Equation 3 below.

$$OC1=C(C=C2C=CNC2=C1)C1=C(C=CC=C1)$$
$$C1=CC2=C(NC=C2)C=C1 \quad \text{[Equation 3]}$$

The factor is an element defining the relationships among the descriptor, the property, and the structure. The factor may be at least one hidden layer. When the factor includes a plurality of hidden layers, a factor defining the relationship between the descriptor and the property, a factor defining the relationship between the descriptor and the structure, and the like may be determined for each hidden layer.

The DNN 410 may be driven by receiving a descriptor as input data and output a property value corresponding to the received descriptor as output data. In a learning process using a descriptor and a property value, the DNN 410 may determine a factor defining the relationship between the descriptor and the property value. The RNN 420 may be driven by receiving a descriptor or a factor determined in a learning process of the DNN 410 as input data and output a structure characteristic value as output data.

Figure 5:
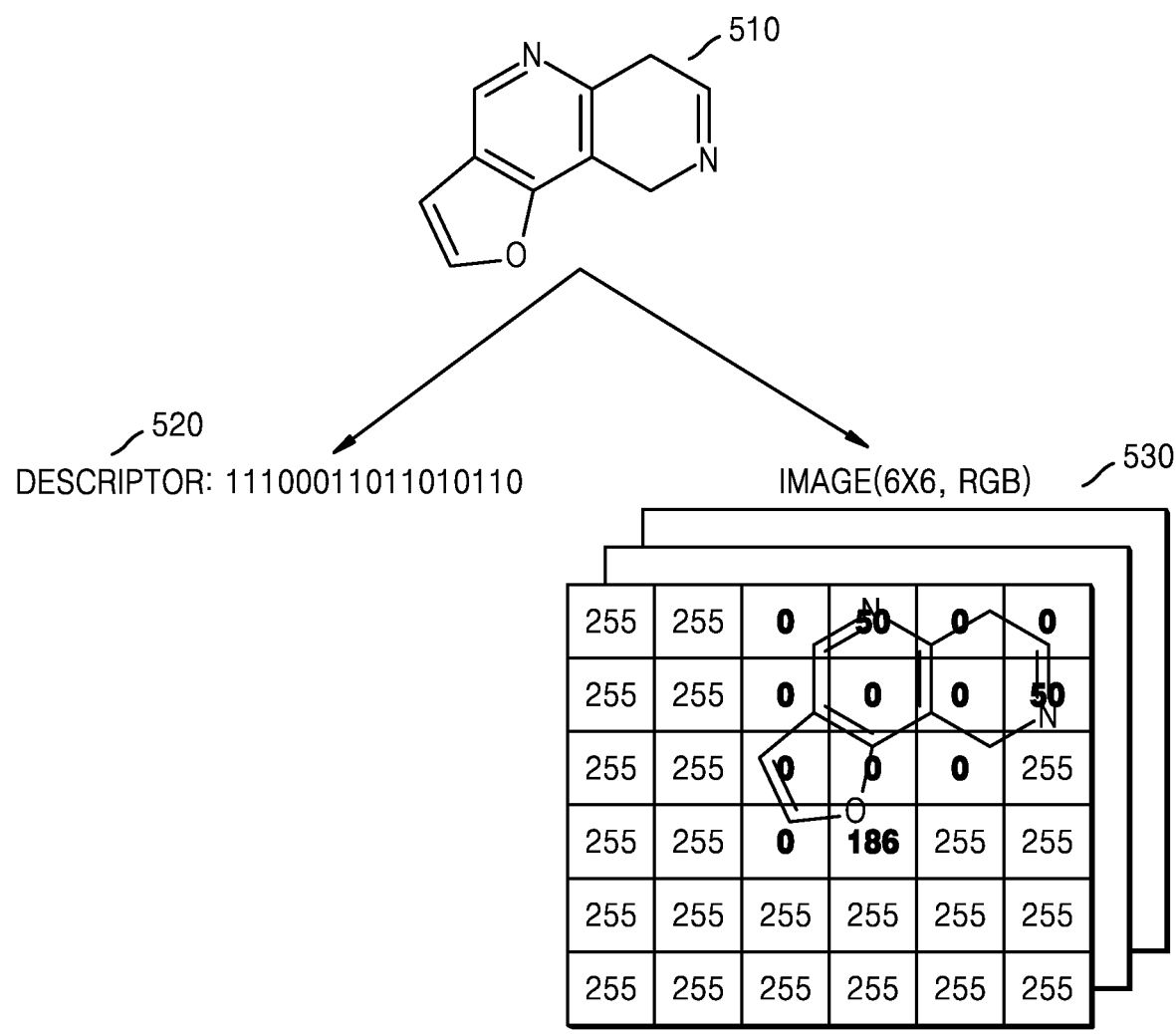
FIG. 5 is a diagram illustrating a method of representing a chemical structure, according to an embodiment.

FIG. 5 is a diagram illustrating a method of representing a chemical structure 510, according to an embodiment.

Referring to FIG. 5, the chemical structure 510 represents the shape of a molecule formed by a combination of atoms. The chemical structure 510 may be represented by the position of an atom, the distance between atoms, the strength of an atomic bond, and the like.

In an embodiment, the chemical structure 510 may be represented by a descriptor 520 including a plurality of bit values (1 or 0). It may be determined whether the chemical structure 510 includes a particular partial structure, through the descriptor 520.

In another embodiment, the chemical structure 510 may be represented as an image 530 having a certain size. The image 530 may include three channels (red, green, and blue (RGB)) of n×m pixels (where n and m are natural numbers). In the image, 8 bits, i.e., a value from 0 (black) to 255 (white), may be assigned to each pixel of the image 530. For example, bright red may be synthesized with an R channel value of 246, a G channel value of 20, and a B channel value of 50, and when all channel values are 255, white is synthesized.

Hereinafter, for convenience of description, a method in which the chemical structure 510 is displayed as an image 530 by using one channel will be described.

Atoms constituting the chemical structure 510 may be displayed in colors that are distinct from each other on the image 530. The chemical structure 510 may include carbon (C), nitrogen (N), and oxygen (O), and on the image 530, the carbon (C) may be displayed in black, the nitrogen (N) may be displayed in blue, and the oxygen (O) may be displayed in red.

Referring to FIG. 5, on the image 530 including 6×6 pixels, the value of a pixel at which the carbon (C) of the chemical structure 510 is located may be '0', the value of a pixel at which the nitrogen (N) is located may be '50', and the value of a pixel at which the oxygen (O) is located may be '186'. The value of a pixel where no atom is present may be '255'.

The color type in which a certain atom is displayed on the image 530, the number of pixels constituting the image 530, and the like are not limited to the above example.

The descriptor 520 or the image 530 for the chemical structure 510 may be used as input data of a neural network, and a particular property value for the chemical structure 510 may be output as output data of the neural network.

Figure 6:
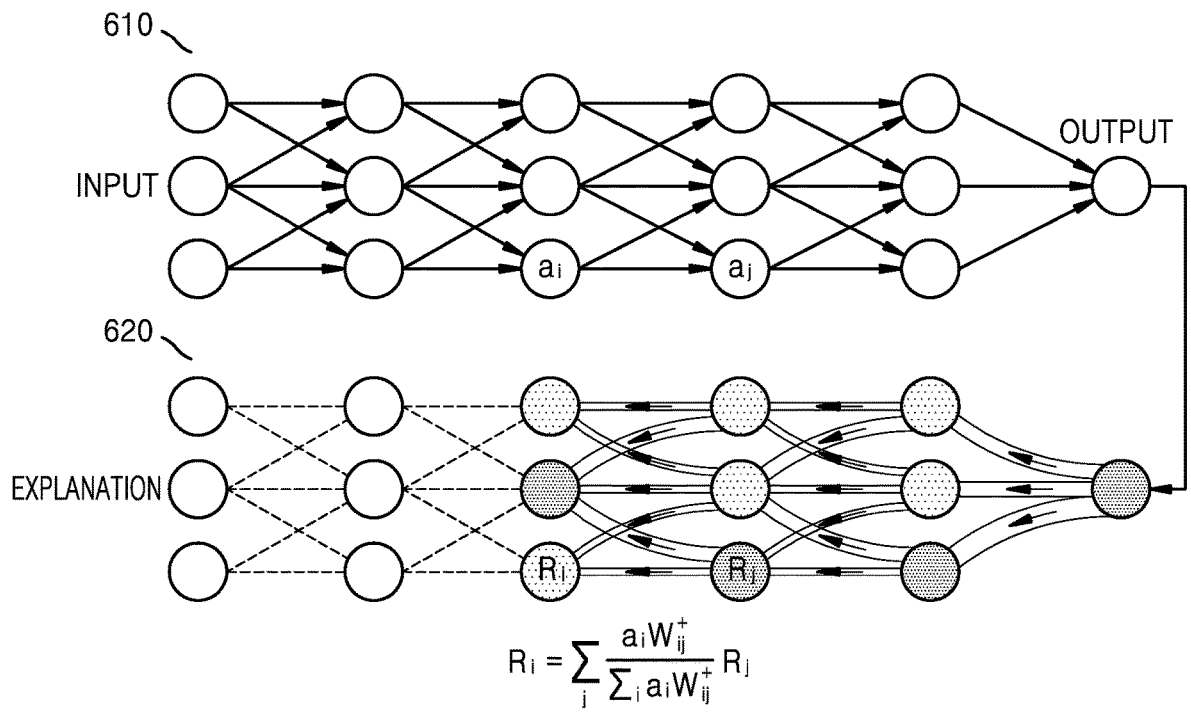
FIG. 6 is a diagram illustrating a method of interpreting a neural network, according to an embodiment.

FIG. 6 is a diagram illustrating a method of interpreting a neural network, according to an embodiment.

The neural network apparatus 100 may obtain a descriptor or image for a reference chemical structure to output a particular property value for the reference chemical structure. In an embodiment, the descriptor may include a plurality of bit values, and the image may include n×m pixels (where n and m are natural numbers).

The neural network apparatus 100 may input the descriptor or image for the reference chemical structure to the trained neural network as input data and drive the neural network, through an inference process 610, to obtain a particular property value for the reference chemical structure as output data of the neural network.

In this case, the neural network apparatus 100 may perform an interpretation process 620 to determine whether a particular property value is expressed by a partial structure in the reference chemical structure.

Referring to FIG. 6, in an embodiment, the neural network apparatus 100 may interpret a trained neural network by using a Layer-wise Relevance Propagation (LRP) technique. The LRP technique is a method of propagating relevance in a reverse direction (i.e., a direction from an output layer to an input layer) of the trained neural network. In the LRP technique, when the relevance is propagated between layers, a node having the greatest relevance to an upper layer among a plurality of nodes of a lower layer obtains the greatest relevance from the corresponding node of the upper layer.

A method of calculating relevance in the LRP technique may be expressed by Equation 4. In Equation 4, as and $a_j$ are an output value to be determined in a particular node of an $i^{th}$ layer and an output value to be determined in a particular node of a $j^{th}$ layer, respectively. $w^+_{ij}$ is a weight value that connects the particular node of the $i^{th}$ layer to the particular node of the $j^{th}$ layer. $R_i$ and $R_j$ denote the relevance of the particular node of the $i^{th}$ layer and the relevance of the particular node of the $j^{th}$ layer, respectively.

$$R_i = \sum_j \frac{a_i w^+_{ij}}{\sum_i a_j w^+_{ij}} R_j \quad \text{[Equation 4]}$$

In an embodiment, for the application of the LRP technique, the neural network apparatus 100 may designate an activation function, applied to a node of a trained neural network, as a linear function by using a regression analysis method, and may designate Mean Square Error (MSE) for optimization. Specifically, in the regression analysis method, because a final output value may include several integer values, the neural network may be trained by designating an activation function of an output node as a linear function. In order to implement the regression analysis method, a loss function may be designated as MSE in a neural network learning process.

However, the technique that may be used in the interpretation process 620 to determine whether a particular property value is expressed by any partial structure in the reference chemical structure is not limited to the example described above.

When the input data of the neural network is a descriptor for the reference chemical structure, a plurality of nodes of the input layer may respectively correspond to bit values constituting the descriptor. The neural network apparatus 100 may obtain a node of the input layer (i.e., a bit position of the descriptor), which has the greatest relevance to the expression of a particular property value of the reference chemical structure, through the interpretation process 620. Because the bit position of the descriptor corresponds to a particular partial structure in the reference chemical structure, the neural network apparatus 100 may determine a particular partial structure, which has the greatest relevance to the expression of a particular property value of the reference chemical structure, by obtaining the bit position of the descriptor through the interpretation process 620.

When the input data of the neural network is an image for the reference chemical structure, the plurality of nodes of the input layer may respectively correspond to pixel values constituting the image. The neural network apparatus 100 may obtain a node of the input layer (i.e., pixel coordinates of the image), which has the greatest relevance to the expression of a particular property value of the reference chemical structure, through the interpretation process 620. Because the pixel coordinates of the image corresponds to a particular partial structure in the reference chemical structure, the neural network apparatus 100 may determine a particular partial structure, which has the greatest relevance to the expression of a particular property value of the reference chemical structure, by obtaining the pixel coordinates of the image through the interpretation process 620.

Hereinafter, the bit position of the descriptor and the pixel coordinates of the image, which have the greatest relevance to the expression of a particular property value of the reference chemical structure, will be referred to as an expression region.

Figure 7:
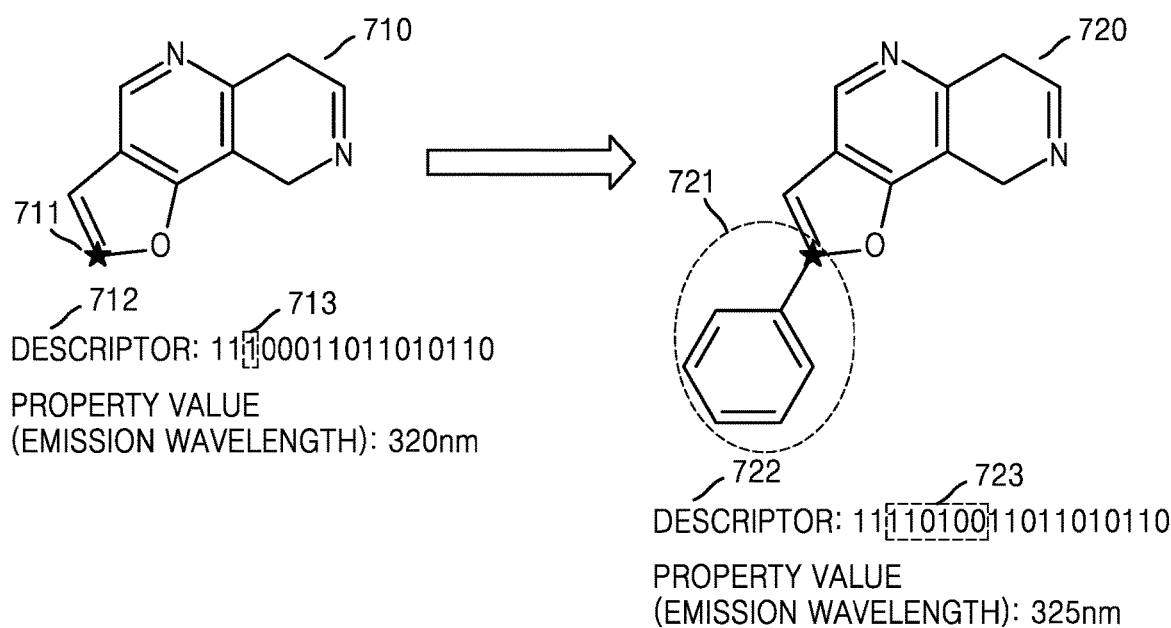
FIG. 7 is a diagram illustrating an example of changing an expression region of a descriptor to generate a new chemical structure according to an embodiment.

FIG. 7 is a diagram illustrating an example of changing an expression region of a descriptor to generate a new chemical structure according to an embodiment.

Referring to FIG. 7, a descriptor 712 of a reference chemical structure 710 may be '11100011011010110'. The neural network apparatus 100 may sequentially input bit values constituting the descriptor 712 respectively to nodes of an input layer of the neural network (e.g., DNN) and output a property value (i.e., an 'emission wavelength: 320 nm') for the reference chemical structure 710.

The neural network apparatus 100 may obtain a node of the input layer (i.e., an expression region 713 of the descriptor 712), which has the greatest relevance to the expression of a wavelength value of the reference chemical structure 710. The expression region 713 of the descriptor 712 may correspond to a particular position 711 in the reference chemical structure 710. In FIG. 7, the expression region 713 corresponds to one bit value. However, the expression region 713 may correspond to a plurality of consecutive bit values, and a plurality of expression regions may be in the descriptor 712.

The neural network apparatus 100 may change a bit value of the expression region 713 to improve the property of the reference chemical structure 710. The structure of the particular position 711 may be changed as the bit value of the expression region 713 is changed. As a method of changing the bit value of the expression region 713, a genetics algorithm may be used, and the details thereof will be described later with reference to FIG. 8. The neural network apparatus 100 may change the bit value of the expression region 713 and/or a bit value around the expression region 713.

The neural network apparatus 100 may change the bit value of the expression region 713 and output a new descriptor 722. Referring to FIG. 7, as a bit value '1' of the expression region 713 in the new descriptor 722 is changed to '110100', the neural network apparatus 100 may apply a new partial structure 721 corresponding to the bit value '110100' to the particular position 711 and generate a new chemical structure 720 to which the new partial structure 721 is applied.

In connection with a method of generating the new chemical structure 720, the neural network apparatus 100 may input the new descriptor 722 as input data of a neural network (e.g., RNN) and output a structure characteristic value as output data, and may generate the new chemical structure 720 based on the output structure characteristic value.

The neural network apparatus 100 may input the descriptor 722 of the new chemical structure 720 into the neural network and output a property value (i.e., 'emission wavelength: 325 nm') corresponding to the descriptor 722 input into the neural network. That is, the neural network apparatus 100 may improve a property by changing a partial structure of the reference chemical structure 710 and generating the new chemical structure 720.

The neural network apparatus 100 may repeatedly generate a chemical structure through the above-described process until a chemical structure having a property value close to a preset value (e.g., 'emission wavelength: 350 nm') is generated.

Specifically, the neural network apparatus 100 may compare a property value (e.g., 'emission wavelength: 325 nm') for the new chemical structure 720 to a preset value (e.g., 'emission wavelength: 350 nm') and generate a new chemical structure by changing the bit value of the expression region 723 of the descriptor 722 when the property value for the new chemical structure 720 is less than the preset value.

When the property value for the new chemical structure generated through the above-described process is equal to or greater than the preset value, the neural network apparatus 100 may store the generated new chemical structure in a memory.

Figure 8:
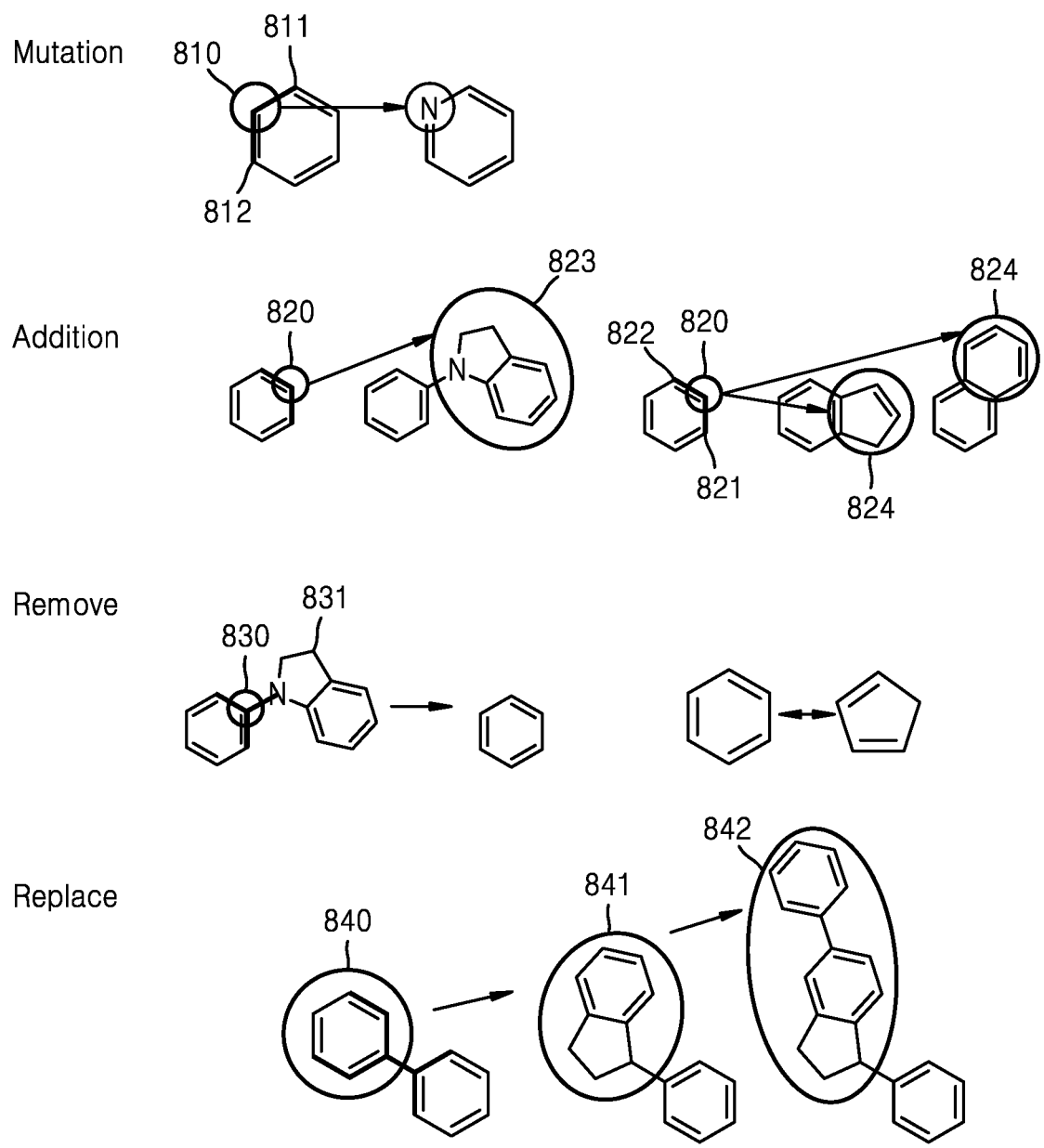
FIG. 8 is a diagram illustrating an example of changing a partial structure by changing a bit value of a descriptor according to an embodiment.

FIG. 8 is a diagram illustrating an example of changing a partial structure by changing a bit value of a descriptor according to an embodiment.

In an embodiment, the neural network apparatus 100 may apply a genetics algorithm to a bit value constituting a descriptor of a reference chemical structure and perform a selection, intersection, or mutation operation on the bit value.

The neural network apparatus 100 may change the descriptor of the reference chemical structure by applying the genetics algorithm to the bit value constituting the descriptor of the reference chemical structure. As the descriptor of the reference chemical structure is changed or modified, a partial structure in the reference chemical structure may be mutated, removed, or replaced, or a partial structure may be added to the reference chemical structure.

Referring to FIG. 8, the neural network apparatus 100 may mutate the partial structure in the reference chemical structure by applying the genetics algorithm to the bit value constituting the descriptor of the reference chemical structure. For example, the neural network apparatus 100 may change carbon (C) in a first position 810 in the reference chemical structure to nitrogen (N). Alternatively, the neural network apparatus 100 may change adjacent atoms 811 and 812 combined with an atom in the first position 810 to other atoms.

In addition, the neural network apparatus 100 may add a partial structure to the reference chemical structure by applying the genetics algorithm to the bit value constituting the descriptor of the reference chemical structure. For example, the neural network apparatus 100 may add a partial structure 823 to be connected to an atom in a second position 820 in the reference chemical structure. Alternatively, the neural network apparatus 100 may add a partial structure to be connected to adjacent atoms 821 and 822 combined with an atom in the second position 820. Alternatively, the neural network apparatus 100 may add a partial structure 824 in the form of a condensed ring, connected to both an atom in the second position 820 and an adjacent atom 821 combined with the atom in the second position 820.

In addition, the neural network apparatus 100 may remove a partial structure in the reference chemical structure by applying the genetics algorithm to the bit value constituting the descriptor of the reference chemical structure. For example, the neural network apparatus 100 may remove a partial structure 831 connected to an atom in a third position 830 in the reference chemical structure. Alternatively, the neural network apparatus 100 may change a ring structure by removing an atom in the third position 830.

In addition, the neural network apparatus 100 may replace a partial structure in the reference chemical structure by applying the genetics algorithm to the bit value constituting the descriptor of the reference chemical structure. For example, the neural network apparatus 100 may change a ring structure of the fourth position 840 in the reference chemical structure to a new partial structure 841 or 842.

However, the example of changing a partial structure by changing the bit value of the descriptor is not limited to the above descriptions.

Figure 9:
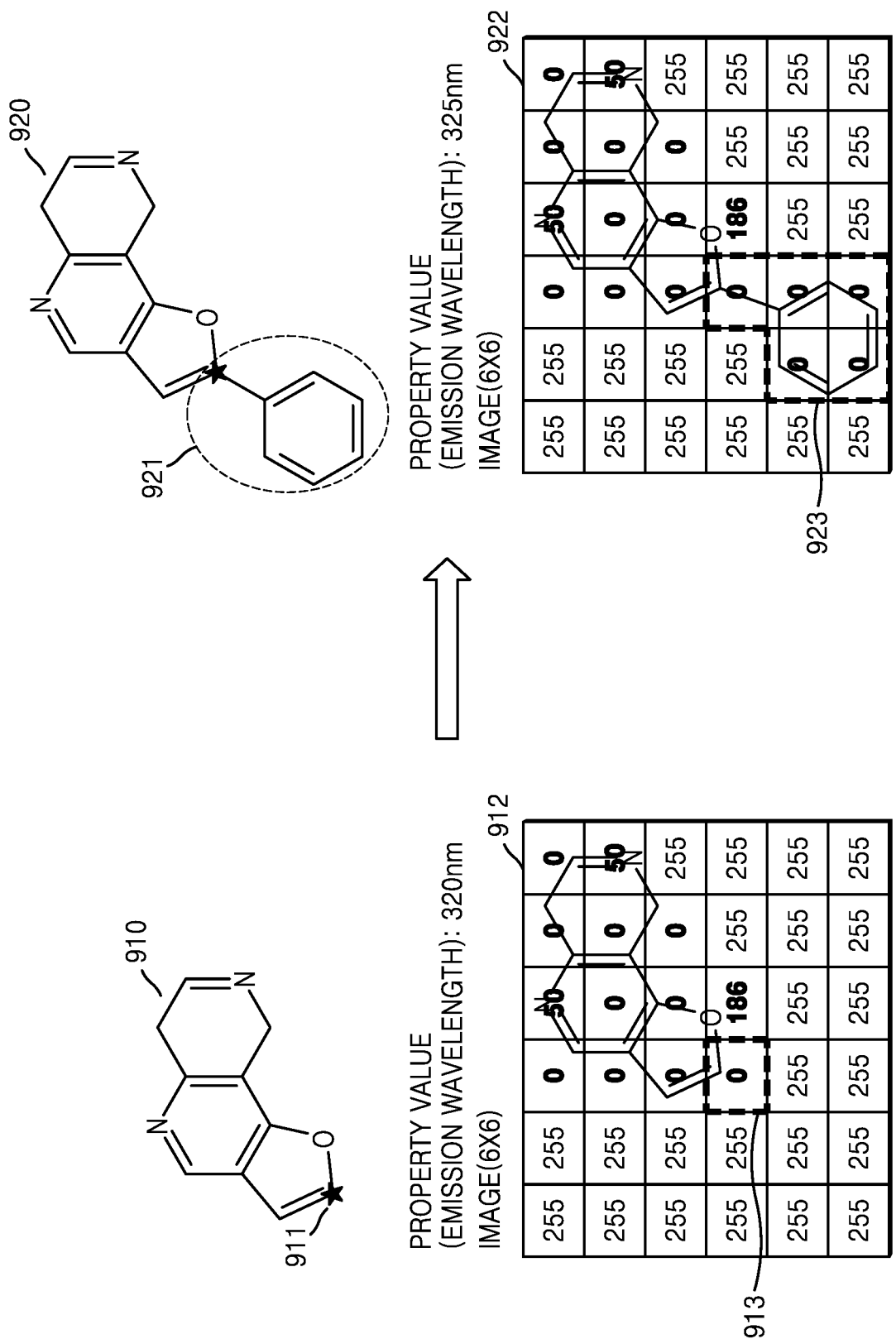
FIG. 9 is a diagram illustrating an example of changing a partial structure by changing a pixel value of an image according to an embodiment.

FIG. 9 is a diagram illustrating an example of changing a partial structure by changing a pixel value of an image according to an embodiment.

Referring to FIG. 9, an image 912 of a reference chemical structure 910 may include 6×6 pixels. Atoms constituting the reference chemical structure 910 may be displayed in colors that are distinct from each other on the image 912. The reference chemical structure 910 may include carbon (C), nitrogen (N), and oxygen (O), and on the image 912, the carbon (C) may be displayed in black, the nitrogen (N) may be displayed in blue, and the oxygen (O) may be displayed in red. On the image 912, the value of a pixel at which the carbon (C) is located may be '0', the value of a pixel at which the nitrogen (N) is located may be '50', and the value of a pixel at which the oxygen (O) is located may be '186'.

The neural network apparatus 100 may sequentially input pixel values constituting the image 912 respectively to nodes of an input layer of a neural network (e.g., DNN) and thus may output a property value (i.e., an 'emission wavelength: 320 nm') for the reference chemical structure 910.

The neural network apparatus 100 may obtain a node of the input layer (i.e., an expression region 913 of the image 912) which has the greatest relevance to the expression of a wavelength value of the reference chemical structure 910. The expression region 913 of the image 912 may correspond to a particular position 911 in the reference chemical structure 910. In FIG. 9, the expression region 913 corresponds to one pixel value. However, the expression region 913 may correspond to a plurality of adjacent pixel values, and a plurality of expression regions may be provided in the image 912.

The neural network apparatus 100 may change a pixel value of the expression region 913 and/or a pixel value around the expression region 913 to improve the property of the reference chemical structure 910. The structure of the particular position 911 may be changed as the pixel value of the expression region 913 and/or the pixel value around the expression region 913 are changed. In an embodiment, the pixel value of the expression region 913 and/or the pixel values around the expression region 913 may be changed by using Gaussian noise. Gaussian noise refers to a noise of which a distribution function of an arbitrary order is represented by a normal distribution.

The neural network apparatus 100 may change the pixel value of the expression region 913 and/or the pixel value around the expression region 913 and thus output a new image 922. Referring to FIG. 9, as the pixel value of the expression region 913 and/or the pixel values around the expression region 913 in the new image 922 are changed, the neural network apparatus 100 may apply a new partial structure 921 corresponding to a changed pixel value to the particular position 911 and generate a new chemical structure 920.

In connection with a method of generating the new chemical structure 920, the neural network apparatus 100 may input the new image 922 as input data of a neural network (e.g., RNN) and output a structure characteristic value as output data, and may generate the new chemical structure 920 based on the output structure characteristic value.

The neural network apparatus 100 may input the image 922 of the new chemical structure 920 into the neural network and output a property value (i.e., 'emission wavelength: 325 nm') corresponding to the image 922 input into the neural network. That is, the neural network apparatus 100 may improve a property by changing a partial structure of the reference chemical structure 910 and generating the new chemical structure 920.

The neural network apparatus 100 may repeatedly generate a chemical structure through the above-described process until a chemical structure having a property value close to a preset value (e.g., 'emission wavelength: 350 nm') is generated.

Specifically, the neural network apparatus 100 may compare a property value (e.g., 'emission wavelength: 325 nm') for the new chemical structure 920 to a preset value (e.g., 'emission wavelength: 350 nm') and generate a new chemical structure by changing the pixel value of the expression region 913 and the pixel value around the expression region 913 in the image 922 when the property value for the new chemical structure 920 is less than the preset value.

When the property value for the new chemical structure generated through the above-described process is equal to or greater than the preset value, the neural network apparatus 100 may store the generated new chemical structure in a memory.

Figure 10:
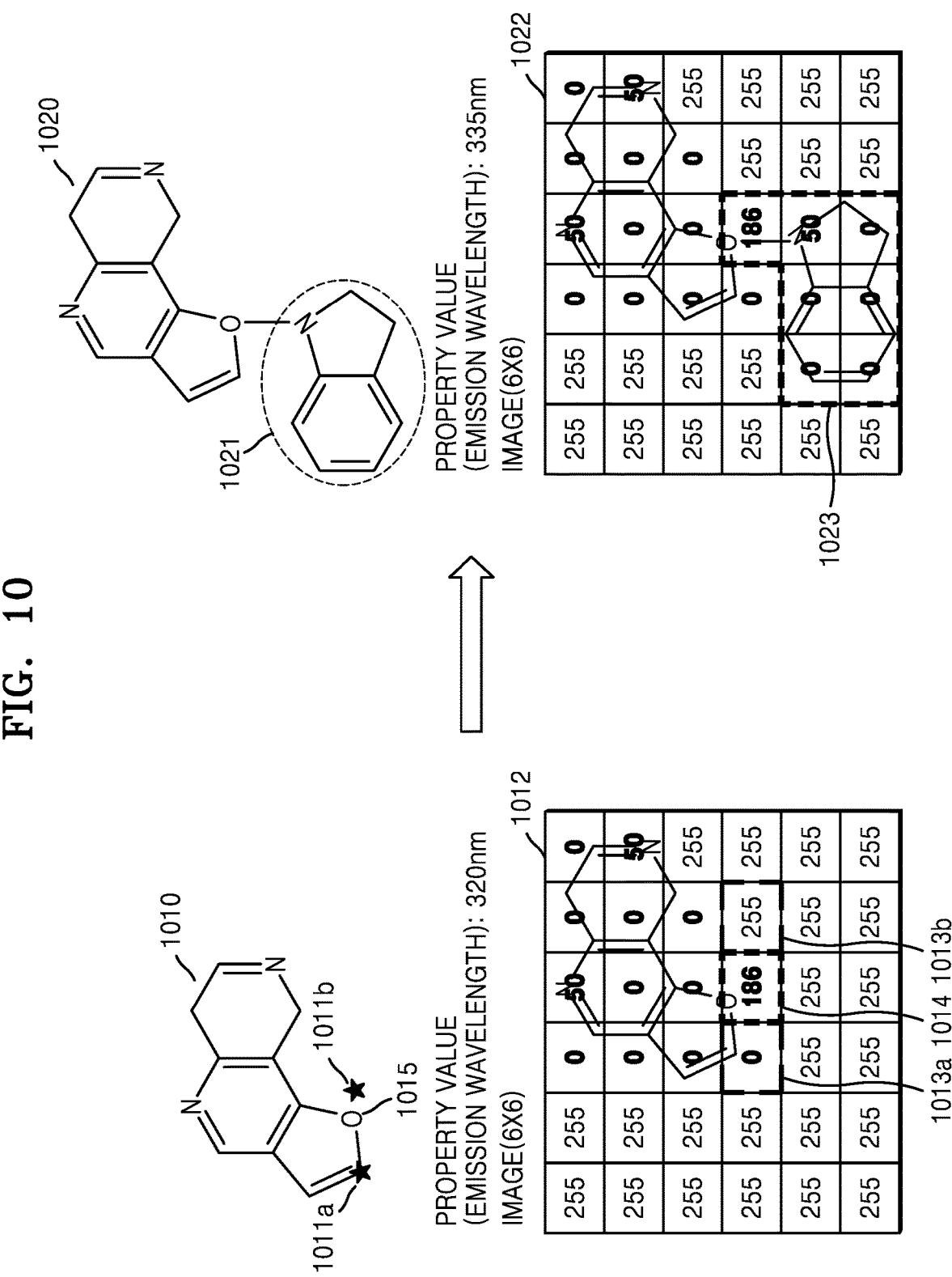
FIG. 10 is a diagram illustrating an example of changing a pixel value when there are a plurality of expression regions on an image according to an embodiment.

FIG. 10 is a diagram illustrating an example of changing a pixel value when there are a plurality of expression regions on an image according to an embodiment.

Referring to FIG. 10, an image 1012 of a reference chemical structure 1010 may include 6×6 pixels. Atoms constituting the reference chemical structure 1010 may be displayed in colors that are distinct from each other on the image 1012. For example, on the image 1012, the value of a pixel at which the carbon (C) is located may be '0', the value of a pixel at which the nitrogen (N) is located may be '50', and the value of a pixel at which the oxygen (O) is located may be '186'.

The neural network apparatus 100 may sequentially input pixel values constituting the image 1012 to nodes of an input layer of a neural network (e.g., DNN) and output a property value (i.e., an 'emission wavelength: 320 nm') for the reference chemical structure 1010.

In an embodiment, there may be multiple nodes of an input layer that have the greatest relevance, or high relevance with respect to other nodes, to the expression of a wavelength value of the reference chemical structure 1010. That is, there may be a plurality of expression regions, i.e., a first expression region 1013a and a second expression region 1013b, on the image 1012. The first expression region 1013a and the second expression region 1013b in the image 1012 may correspond to a first position 1011a and a second position 1011b in the reference chemical structure 1010, respectively. As shown in FIG. 10, the second position 1011b corresponding to the second expression region 1013b may be outside the reference chemical structure 1010.

When there are a plurality of expression regions, i.e., the first expression region 1013a and the second expression region 1013b, on the image 1012, the neural network apparatus 100 may obtain coordinate information on the image 1012, which corresponds to the plurality of expression regions, i.e., the first expression region 1013a and the second expression region 1013b. For example, based on a lower left corner of the image 1012 having the origin (0,0), the coordinate information of the first expression region 1013a may be (3, 3) and the coordinate information of the second expression region 1013b may be (5, 3).

The neural network apparatus 100 may output the coordinate information (4, 3) of a center point 1014 based on the coordinate information corresponding to the plurality of expression regions, i.e., the first expression region 1013a and the second expression region 1013b. The neural network apparatus 100 may change a pixel value of the center point 1014 and/or a pixel value around the center point 1014 to improve the property of the reference chemical structure 1010. As the pixel value of the center point 1014 and/or the pixel value around the center point 1014 are changed, the structure of a particular position 1015 on the reference chemical structure 1010 corresponding to the center point 1014 may be changed. In an embodiment, the pixel value of the center point 1014 and/or the pixel value around the center point 1014 may be changed by using Gaussian noise.

The neural network apparatus 100 may change the pixel value of the center point 1014 and/or the pixel value around the center point 1014 and output a new image 1022. Referring to FIG. 10, as the pixel value of the center point 1014 and/or the pixel value around the center point 1014 in the new image 1022 are changed, the neural network apparatus 100 may apply a new partial structure 1021 corresponding to a changed pixel value to the particular position 1015 and generate a new chemical structure 1020.

The neural network apparatus 100 may input the image 1022 of the new chemical structure 1020 into the neural network and output a property value (i.e., 'emission wavelength: 325 nm') corresponding to the image 1022 input into the neural network. That is, the neural network apparatus 100 may improve a property by changing a partial structure of the reference chemical structure 1010 and generating the new chemical structure 1020.

Figure 11:
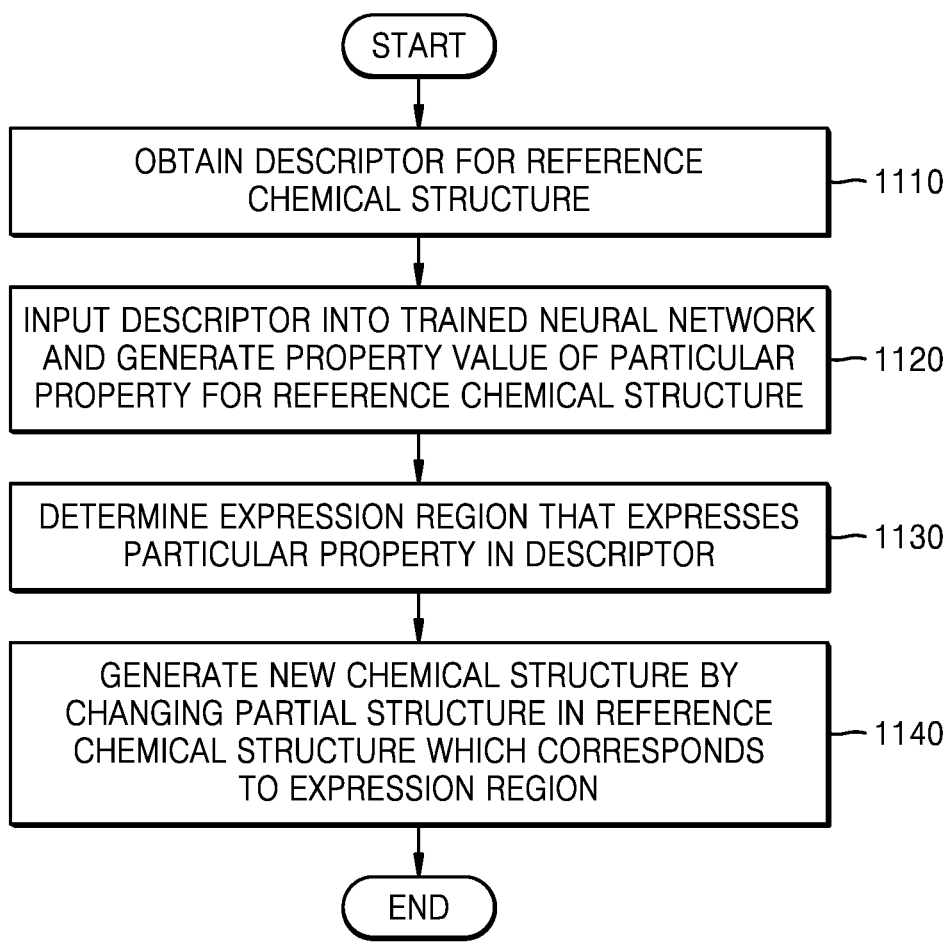
FIG. 11 is a flowchart of a method of generating a new chemical structure by changing a descriptor for a chemical structure in a neural network apparatus, according to an embodiment.

FIG. 11 is a flowchart of a method of generating a new chemical structure by changing a descriptor for a chemical structure in a neural network apparatus according to an embodiment.

The method of generating a chemical structure in a neural network apparatus relates to the embodiments described above with reference to the drawings, and thus, although omitted in the following descriptions, descriptions given above with reference to the drawings may also be applied to the method illustrated in FIG. 11.

Referring to FIG. 11, in operation 1110, the neural network apparatus may obtain a descriptor for a reference chemical structure.

The descriptor is an indicator value used to represent the structural characteristics of a chemical structure. The descriptor may be obtained by performing a relatively simple operation on a given chemical structure. In an embodiment, the descriptor may be represented by an ECFP and may include a plurality of bit values. However, the manner of expression of the descriptor is not limited thereto.

Hereinafter, the descriptor for the reference chemical structure will be referred to as a reference descriptor.

In operation 1120, the neural network apparatus may input a reference descriptor into a trained neural network and output a property value of a particular property for the reference chemical structure.

The property refers to a characteristic possessed by a chemical structure and may be a real number value indicating a transmission wavelength and an emission wavelength with respect to light. Unlike the case of the descriptor, the computation of the property may require complex simulations and be time consuming.

A memory of the neural network apparatus may store a descriptor for a particular chemical structure and a property value numerically representing the property of the particular chemical structure, which match each other as one set.

In an embodiment, the neural network apparatus may allow a neural network (e.g., DNN) to learn by using a descriptor and a property value, stored in a memory. In a learning process using the descriptor and the property value, a factor defining the relationship between the descriptor and the property value may be determined in the neural network.

The neural network apparatus may output a property value corresponding to the reference descriptor as output data of the neural network by inputting the reference descriptor as input data of the trained neural network and driving the neural network.

In operation 1130, the neural network apparatus may determine an expression region that expresses a particular property in the reference descriptor.

The neural network apparatus may perform an interpretation process to determine whether a particular property value is expressed by any partial structure in the reference chemical structure.

In an embodiment, the neural network apparatus may interpret the trained neural network by using an LRP technique. The LRP technique is a method of propagating relevance in a reverse direction (i.e., a direction from an output layer to an input layer) of the trained neural network. In the LRP technique, when the relevance is propagated between layers, a node having the greatest relevance to an upper layer among a plurality of nodes of a lower layer obtains the greatest relevance from the corresponding node of the upper layer.

For the application of the LRP technique, the neural network apparatus may designate an activation function, applied to a node of the trained neural network, as a linear function, and may designate MSE for optimization.

A plurality of nodes of the input layer of the neural network may respectively correspond to bit values constituting the descriptor. The neural network apparatus may obtain a node of the input layer, i.e., a bit position (or expression region) of the reference descriptor, which has the greatest relevance in the expression of a particular property value of the reference chemical structure, through the interpretation process. Because the expression region of the reference descriptor corresponds to a particular partial structure in the reference chemical structure, the neural network apparatus may determine a particular partial structure, which has the greatest relevance in the expression of a particular property value of the reference chemical structure, by obtaining the expression region of the reference descriptor through the interpretation process.

In operation 1140, the neural network apparatus may generate a new chemical structure by changing a partial structure in the reference chemical structure which corresponds to the expression region.

The neural network apparatus may receive a target property value as an input. In an embodiment, the neural network apparatus may include a user interface that is a means for inputting data for controlling the neural network apparatus. For example, the user interface may be a key pad, a touch pad, or the like, but is not limited thereto.

The target property value is a numerical value of a particular property of a chemical structure to be finally generated in the neural network apparatus. In an embodiment, the target property value may be a refractive index value, an elastic modulus, a melting point, a transmission wavelength, and/or an emission wavelength. For example, the neural network apparatus may receive 'emission wavelength: 350 nm' as a target property value. Alternatively, the target property value may be set in an increasing (+) direction or a decreasing (−) direction rather than a numerical value.

The neural network apparatus may generate a new chemical structure having a property value close to the target property value by changing a partial structure in the reference chemical structure.

In an embodiment, the neural network apparatus may output a new descriptor by changing a bit value of an expression region of the reference descriptor. The partial structure in the reference chemical structure may be changed as the bit value of the expression region of the reference descriptor is changed. A method of changing the bit value of the expression region may use a genetics algorithm, but is not limited thereto.

The neural network apparatus may output a structure characteristic value corresponding to the new descriptor as output data of the neural network by inputting the new descriptor, in which the bit value of the expression region of the reference descriptor is changed, as input data of the trained neural network (e.g., RNN) and driving the neural network. The neural network apparatus may generate a new chemical structure based on the output structure characteristic value. Alternatively, the neural network apparatus may use a factor for the new descriptor, output in a learning process of the DNN, as input data of the trained neural network (e.g., RNN).

The neural network apparatus may iteratively generate a chemical structure through the above-described process until a chemical structure having a property value close to a target property value (e.g., 'emission wavelength: 350 nm') is generated.

Specifically, the neural network apparatus may compare a property value for a new chemical structure to a target property value and generate a new chemical structure again by changing the bit value of the expression region of the reference descriptor when the property value for the new chemical structure is less than the target property value.

When the property value of the new chemical structure generated through the above-described process is equal to or greater than the target property value, the neural network apparatus may store the generated new chemical structure in a memory.

Figure 12:
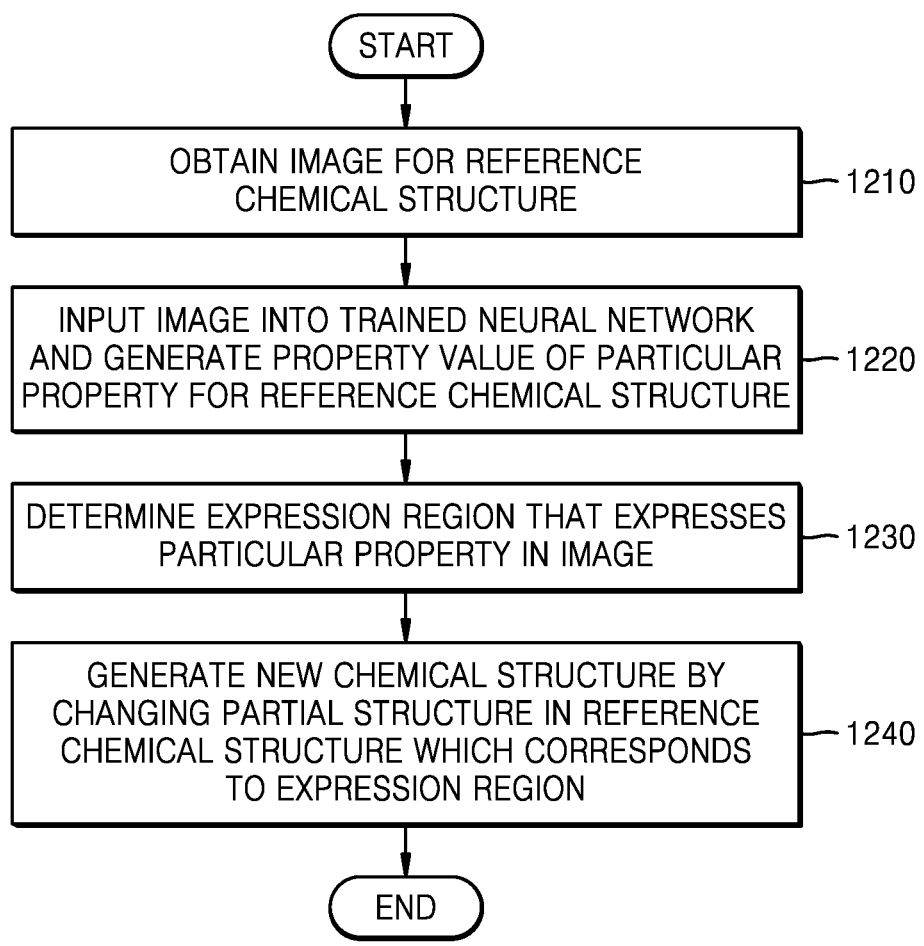
FIG. 12 is a flowchart of a method of generating a new chemical structure by changing an image for a chemical structure in a neural network, apparatus according to an embodiment.

FIG. 12 is a flowchart of a method of generating a new chemical structure by changing an image for a chemical structure in a neural network apparatus according to an embodiment.

Hereinafter, descriptions that are the same as those given with reference to FIG. 11 are omitted.

Referring to FIG. 12, in operation 1210, the neural network apparatus may obtain an image for a reference chemical structure.

In an embodiment, the image for the reference chemical structure may include n×m pixels (where n and m are natural numbers). For example, 8 bits, i.e., a value from 0 (black) to 255 (white), may be assigned to each pixel of the image.

Hereinafter, the image for the reference chemical structure will be referred to as a reference image.

In operation 1220, the neural network apparatus may input the reference image into a trained neural network and output a property value of a particular property for the reference chemical structure.

A memory of the neural network apparatus may store an image for a particular chemical structure and a property value numerically representing the property of the particular chemical structure, which match each other as one set.

In an embodiment, the neural network apparatus may allow a neural network (e.g., DNN) to learn by using an image and a property value, stored in a memory. In a learning process using the image and the property value, a factor defining the relationship between the image and the property value may be determined in the neural network.

The neural network apparatus may output a property value corresponding to the reference image as output data of the neural network by inputting the reference image as input data of the trained neural network and driving the neural network.

In operation 1230, the neural network apparatus may determine an expression region that expresses a particular property in the image.

A plurality of nodes of an input layer of the neural network may respectively correspond to pixel values constituting the image. The neural network apparatus may obtain a node of the input layer, i.e., pixel coordinates (or expression region) of the reference image, which has the greatest relevance in the expression of a particular property value of the reference chemical structure, through the interpretation process. Because the expression region of the reference image corresponds to a particular partial structure in the reference chemical structure, the neural network apparatus may determine a particular partial structure, which has the greatest relevance in the expression of a particular property value of the reference chemical structure, by obtaining the expression region of the reference image through the interpretation process.

In operation 1240, the neural network apparatus may generate a new chemical structure by changing a partial structure in the reference chemical structure which corresponds to the expression region.

In an embodiment, the neural network apparatus may generate a new image by changing a pixel value of the expression region of the reference image and/or a pixel value around the expression region. A partial structure in the reference chemical structure may be changed as the pixel value of the expression region of the reference image and/or the pixel value around the expression region are changed. In an embodiment, the pixel value of the expression region of the reference image and/or the pixel value around the expression region may be changed by using Gaussian Noise, but a method of changing the pixel value is not limited thereto.

The neural network apparatus may output a structure characteristic value corresponding to the new image as output data of the neural network by inputting the new image, in which the pixel value of the expression region of the reference image and/or the pixel value around the expression region are changed, as input data of the trained neural network (e.g., RNN) and driving the neural network. The neural network apparatus may generate a new chemical structure based on the output structure characteristic value. Alternatively, the neural network apparatus may use a factor for the new image, output in a learning process of the DNN, as input data of the trained neural network (e.g., RNN).

The neural network apparatus may iteratively generate a chemical structure through the above-described process until a chemical structure having a property value close to a target property value (e.g., 'emission wavelength: 350 nm') is generated.

Specifically, the neural network apparatus may compare a property value for a new chemical structure to a target property value and generate a new chemical structure again by changing the pixel value of the expression region of the reference image and/or the pixel value around the expression region when the property value for the new chemical structure is less than the target property value.

When the property value of the new chemical structure generated through the above-described process is equal to or greater than the target property value, the neural network apparatus may store the generated new chemical structure in a memory.

According to the aforementioned embodiments, a trained neural network may be interpreted to specify a partial structure expressing a property of a chemical structure. In addition, a new chemical structure having an improved property may be generated by changing the specified partial structure.

Also, the aforementioned embodiments may be embodied in the form of a recording medium storing instructions executable by a computer, such as a program module, executed by a computer. The computer-readable medium may be any recording medium that may be accessed by a computer and may include volatile and non-volatile media and removable and non-removable media. Also, the computer-readable medium may include computer storage media and communication media. The computer storage media include volatile and non-volatile and removable and non-removable media implemented using any method or technology to store information such as computer-readable instructions, data structures, program modules, or other data. The communication media include computer-readable instructions, data structures, program modules, or other data in a modulated data signal, or other transport mechanisms and include any delivery media.

In addition, throughout the specification, the term "unit" may be a hardware component such as a processor or a circuit and/or a software component executed by the hardware component such as a processor.

The above description of the disclosure is provided for the purpose of illustration, and it would be understood by those skilled in the art that various changes and modifications may be made without changing technical conception and essential features of the disclosure. Thus, it is clear that the above-described illustrative embodiments are illustrative in all aspects and do not limit the disclosure. For example, each component described to be of a single type may be implemented in a distributed manner. Likewise, components described to be distributed may be implemented in a combined manner.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of generating a chemical structure by using a neural network apparatus, the method comprising:
    inputting a descriptor of a chemical structure to a trained neural network that generates a property value of a property of the chemical structure, the descriptor of the chemical structure representing structural characteristics of the chemical structure and the property of the chemical structure being a characteristic possessed by the chemical structure;
    determining an expression region for expressing the property in the descriptor, the expression region comprising a first bit position in the descriptor, wherein the descriptor comprises the expression region and a second bit position outside the expression region; and
    generating a new chemical structure by modifying a partial structure in the chemical structure, the partial structure corresponding to the expression region,
    wherein the determining the expression region comprises the determining the expression region by applying a layer-wise relevance propagation (LRP) technique to a deep neural network in the trained neural network.

2. The method of claim 1, wherein an activation function applied to a node of the trained neural network is designated as a linear function to apply the LRP technique to the trained neural network, and a mean square error (MSE) is designated for optimization.

3. The method of claim 1, wherein the generating comprises:
    obtaining a bit value of the bit position of the expression region in the descriptor; and
    generating the new chemical structure by applying a genetics algorithm to the bit value of the bit position and modifying the partial structure corresponding to the expression region.

4. The method of claim 1, wherein the generating comprises:
    generating a new first chemical structure by modifying the partial structure in the chemical structure, the partial structure corresponding to the expression region;
    inputting a descriptor for the new first chemical structure to the trained neural network to output a property value of a particular property for the new first chemical structure; and
    generating a new second chemical structure by changing a partial structure in the new first chemical structure, the partial structure corresponding to the expression region, when the property value of the particular property for the new first chemical structure is less than a preset value, and storing the new first chemical structure when the property value of the particular property for the new first chemical structure is equal to or greater than the preset value.

5. A non-transitory computer-readable recording medium comprising a program, which, when executed by a computer, performs the method of claim 1.

6. A neural network apparatus configured to generate a chemical structure, the neural network apparatus comprising:
    a memory configured to store at least one program; and
    a processor configured to control the neural network apparatus to implement a neural network by executing the at least one program, wherein, when the at least one program is executed, the processor is configured to:
        input a descriptor of a chemical structure to a trained neural network that generates a property value of a property of the chemical structure, the descriptor of the chemical structure representing structural characteristics of the chemical structure and the property of the chemical structure being a characteristic possessed by the chemical structure;
        determine an expression region for expressing the property in the descriptor, the expression region comprising a first bit position in the descriptor, wherein the descriptor comprises the expression region and a second bit position outside the expression region; and
        generate a new chemical structure by modifying a partial structure in the chemical structure, the partial structure corresponding to the expression region,
    wherein the processor is further configured to determine the expression region by applying a layer-wise relevance propagation (LRP) technique to a deep neural network in the trained neural network.

7. The neural network apparatus of claim 6, wherein the processor when the at least one program is executed is further configured to:
    designate an activation function applied to a node of the trained neural network as a linear function to apply the LRP technique to the trained neural network and designate a mean square error (MSE) for optimization.

8. The neural network apparatus of claim 6, wherein the processor when the at least one program is executed is further configured to obtain a bit value of the bit position of the expression region in the descriptor and to generate the new chemical structure by applying a genetics algorithm to the bit value of the bit position and modifying the partial structure corresponding to the expression region.

9. The neural network apparatus of claim 6, wherein the processor when the at least one program is executed is configured to:
    generate a new first chemical structure by modifying the partial structure in the chemical structure, the partial structure corresponding to the expression region;
    input a descriptor for the new first chemical structure to the trained neural network to output a property value of a particular property for the new first chemical structure; and
    generate a new second chemical structure by changing a partial structure in the new first chemical structure, the partial structure corresponding to the expression region, when the property value of the particular property for the new first chemical structure is less than a preset value, and store the new first chemical structure in the memory when the property value of the particular property for the new first chemical structure is equal to or greater than the preset value.

* * * * *